US011208624B2

(12) United States Patent
Bohm et al.

(10) Patent No.: US 11,208,624 B2
(45) Date of Patent: Dec. 28, 2021

(54) DEVICE FOR CENTERING OF PETRI DISHES

(71) Applicant: CLEVER CULTURE SYSTEMS AG, Bach (CH)

(72) Inventors: Alexander Bohm, Klagenfurt am Worthersee (AT); Nedim Bogilovic, Klagenfurt am Worthersee (AT); Wolfgang Stiegmaier, Klagenfurt am Worthersee (AT)

(73) Assignee: CLEVER CULTURE SYSTEMS, AG, Bach (CH)

(*) Notice: Subject to any disclaimer, the term of this patent is extended or adjusted under 35 U.S.C. 154(b) by 330 days.

(21) Appl. No.: 16/090,899

(22) PCT Filed: Mar. 13, 2017

(86) PCT No.: PCT/EP2017/055787
§ 371 (c)(1),
(2) Date: Oct. 3, 2018

(87) PCT Pub. No.: WO2017/174298
PCT Pub. Date: Oct. 12, 2017

(65) Prior Publication Data
US 2019/0119622 A1 Apr. 25, 2019

(30) Foreign Application Priority Data

Apr. 4, 2016 (EP) .................................. 16163699

(51) Int. Cl.
B01L 9/00 (2006.01)
C12M 1/00 (2006.01)
C12M 1/22 (2006.01)
(52) U.S. Cl.
CPC .............. C12M 23/50 (2013.01); B01L 9/52 (2013.01); C12M 23/10 (2013.01)

(58) Field of Classification Search
CPC ........... B01L 9/52; C12M 23/10; C12M 23/50
(Continued)

(56) References Cited

U.S. PATENT DOCUMENTS 3,844,896 A * 10/1974 Sharpe ................... C12M 41/36
435/286.4
4,572,067 A 2/1986 Fischer
(Continued)

FOREIGN PATENT DOCUMENTS

DE 102010044125 A1 * 5/2012 ............ C12M 23/10
EP 2482079 A2 8/2012
(Continued)

OTHER PUBLICATIONS

Kruetzmann Guido, "English machine translation of DE-102010044125-A1".*
(Continued)

Primary Examiner — Liban M Hassan
(74) Attorney, Agent, or Firm — Workman Nydegger

(57) ABSTRACT

A device for centering of petri dishes, where the petri dishes include a bottom container with a lateral surface and a lid with a lid diameter, including an elevator with an elevator axis and an elevator drive, and the conveyor includes concentrically along the elevator axis a frustoconical through-hole tapering downwards, and the elevator drive is built to move a substantially flat plate from a neutral position downwards into a first position, which is reached as soon as the petri dish rests with its weight on the inner surface of the through-hole, and the elevator drive is built to rotate the plate during a movement of the plate from the neutral position into the first position.

6 Claims, 2 Drawing Sheets

(58) Field of Classification Search
USPC .................................................. 435/286.3
See application file for complete search history.

(56) References Cited

U.S. PATENT DOCUMENTS

| | | | |
|---|---|---|---|
| 8,561,376 B2* | 10/2013 | Brelivet | ............... C12M 99/00 |
| | | | 53/250 |
| 2012/0251275 A1* | 10/2012 | Malin | ............... G01N 35/0099 |
| | | | 414/225.01 |
| 2014/0030802 A1 | 1/2014 | Eberle | |

FOREIGN PATENT DOCUMENTS

| | | | | |
|---|---|---|---|---|
| GB | 2511727 A | | 9/2014 | |
| JP | 06225753 A | * | 8/1994 | ............ C12M 23/50 |
| WO | WO 2008/083440 A1 | | 7/2008 | |

OTHER PUBLICATIONS

Written Opinion and International Search Report of PCT/EP2017/055787 dated Apr. 12, 2017.

* cited by examiner

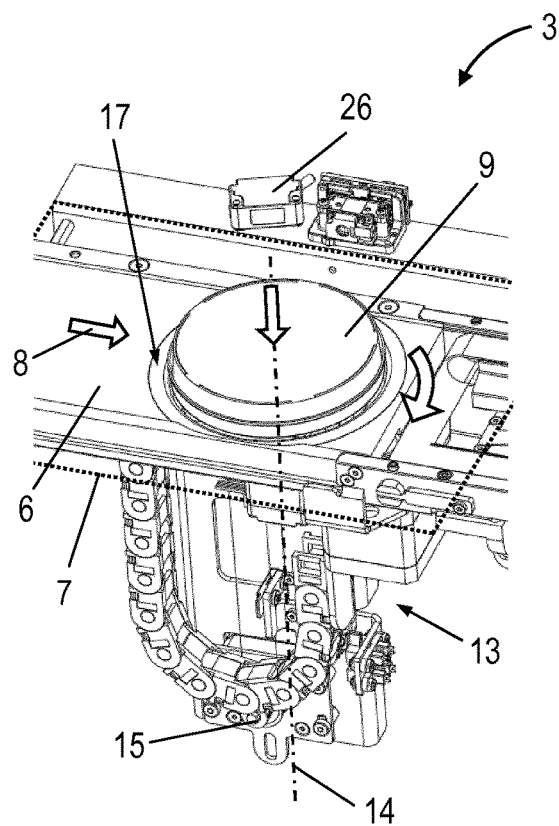
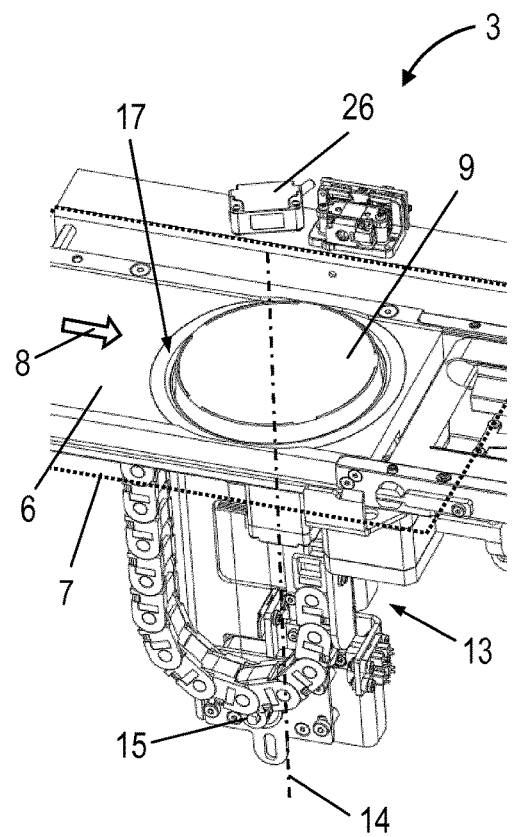
FIG. 3A　　　　　　　　FIG. 3B
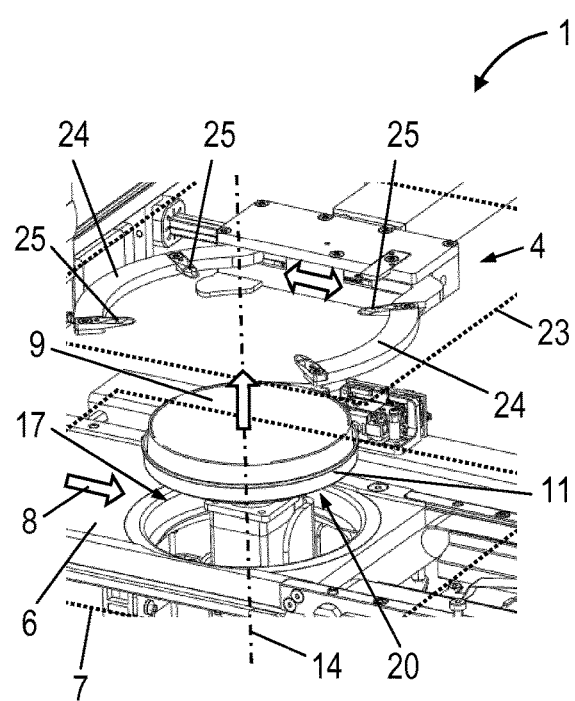
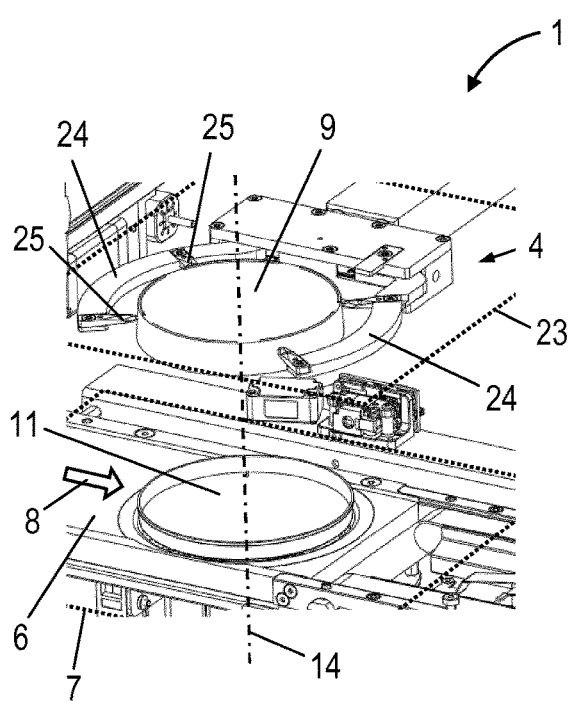
FIG. 4A　　　　　　　　FIG. 4B

DEVICE FOR CENTERING OF PETRI DISHES

CROSS REFERENCE TO RELATED APPLICATIONS

The present application is a U.S. National Stage of International Application No. PCT/EP2017/055787, filed on Mar. 13, 2017, designating the United States and claiming the priority of European Patent Application No. 16163699.8 filed with the European Patent Office on Apr. 4, 2016. All of the aforementioned applications are incorporated herein in their respective entireties by this reference.

FIELD OF THE INVENTION

The present invention is related to a device for centring of petri dishes, which petri dishes consist of a bottom container with a lateral surface and a lid with a lid diameter, comprising an elevator with an elevator axis and an elevator drive, by which the elevator is movable along the elevator axis, and a conveyor, which holds the petri dishes on a conveyor plane substantially rectangular to the elevator axis.

The present invention is furthermore related to a method for centring and handling of petri dishes with a device comprising an elevator movable along an elevator axis by an elevator drive and a conveyor, which holds the petri dish on a conveyor plane and comprises concentrically along the elevator axis a frustoconical through-hole tapering downwards.

BACKGROUND

Petri dishes are flat, circular and transparent containers with an overlapping lid used in biology, medicine or chemistry for the cultivation of microorganisms and cell cultures. A shallow layer of gel growth medium applied onto the bottom of the container supplies the microorganisms with water and nutrients. In general, petri dishes are stored and handled with the lid down and the container upwards in order to improve the closure between the lid and the container and to accumulate excess water in the lid. During an incubation period or an analysis of the cell cultures, they frequently need to be visually inspected. Thus, there is a high need for process automation, especially regarding handling and visual inspection of petri dishes.

EP 2 482 079 A2 discloses a handling system for petri dishes, comprising a handling device in order to move a petri dish to a transfer station, and a gripper in order to take over the container of the petri dish from the transfer station and move the container into a visual inspection unit.

This known handling system has the disadvantage that it is very complex and requires a lot of space and investment. In addition the related handling and movement of the petri dishes is very complicated and thus unsafe and slow.

Summary of Some Aspects of Example Embodiments

Consequently, it is an objective of the presented invention to provide an improved system that saves space and investment and that allows to handle and move petri dishes in a very fast, simple and safe way.

This objective is achieved with a conveyor that comprises concentrically along the elevator axis a frustoconical through-hole tapering downwards from a first opening, which is located in the conveyor plane and is larger than the lid diameter of the petri dish, to a second opening, which is smaller than the lid diameter of the petri dish, and that the elevator drive is built to move a substantially flat plate, which is built to receive the petri dish, from a neutral position located in the conveyor plane downwards into a first position, which is reached as soon as the petri dish rests with its weight on the inner surface of the through-hole, wherein the elevator drive is built to rotate the plate around the elevator axis in order to rotate the plate during a movement of the plate from the neutral position into the first position.

It is furthermore an objective of the presented invention to provide a method that allows to handle and move petri dishes in a very fast, simple and safe way.

This objective is achieved with a method that comprises the following steps:

Move the petri dish on the conveyor plane along a conveyor direction onto a plate of the elevator, wherein the plate is in a neutral position;

Rotate the plate and simultaneously move the plate downwards along the elevator axis through the through-hole until the plate is in a first position, which is reached as soon as the petri dish rests with its weight on the inner surface of the through-hole;

Move the plate from the first position and via the neutral position upwards along the elevator axis through the through-hole until the plate is in a second position, which is reached as soon as a lateral surface of the bottom container lies in a gripper plane of a gripper;

Take over the bottom container of the petri dish from the plate by the gripper.

The device according to the invention comprises the advantage that petri dishes of advantageously circular form and basically any size can be centred in a very fast, safe and simple way. Hereby, the elevator drive of the elevator is advantageously built to rotate the plate and simultaneously move the plate from a neutral position along the elevator axis through the frustoconical through-hole. Thus, a petri dish, which was placed on the plate eccentrically, automatically centres itself by means of the inner surface of the frustoconical through-hole while being moved downwards in a rotating manner. As soon as the petri dish rests with its weight on the inner surface of the frustoconical through-hole, the petri dish is perfectly centred in accordance to the elevator axis, whereas the plate of the elevator is in its first position.

In an advantageous embodiment, the elevator drive is built to move the plate from the first position upwards through the frustoconical through-hole and via the neutral position into a second position, which is reached as soon as the lateral surface of the bottom container lies in the gripper plane. Thus, the whole movement of the petri dish, from its input onto the plate of the elevator to its possible take over, for example by the gripper, is being accomplished along the elevator axis, which advantageously prevents the petri dish from decentring again and allows to speed up the overall handling procedure. In addition, since the petri dish rests on the substantially flat plate of the elevator, the gripper can very easily take over the petri dish within the gripper plane without a need to additionally move along or parallel to the elevator axis, which again allows speeding up the overall handling procedure.

In a further advantageous embodiment, the elevator drive is built to move the plate from the second position downwards into the neutral position in the conveyor plane. Thus, for example after the petri dish was analyzed visually and put back on the plate of the elevator, the petri dish can be moved or processed further very fast, safe and simple.

Hence the advantage is given, that, apart from its movement along the elevator axis and in the gripper plane, the complete movement of the petri dish into the device onto the plate of the elevator and off the plate out from the device can be accomplished on the conveyor plane. This reduces possible tilting and rotating of the petri dish and allows speeding up accompanied handling procedures.

Advantageously, the conveyor comprises a conveyor drive built to convey the petri dishes on the conveyor plane along a conveyor direction onto the plate of the elevator. Thus, the movement of the petri dishes onto the plate of the elevator can be automated. In addition, a petri dish that, for example, has been visually inspected already can be automatically pushed off the plate of the elevator by a new petri dish being moved onto the plate by the conveyor drive, wherein the plate is in its neutral position.

Advantageously, the device according to the invention comprises a first sensor built to detect the petri dish on the plate of the elevator. This has the advantage that the device automatically detects a petri dish received by the plate of the elevator in order to, for example, automatically start the centring of the petri dish.

Advantageously, the device according to the invention is part of a system for handling and centring of petri dishes. The system comprises the gripper with at least two gripper arms movable in the gripper plane towards each other. The gripper is built to receive the bottom container of the petri dish from the plate in its second position by means of applying a lateral force with the gripper arms onto the lateral surface of the bottom container. Thus, the whole handling procedure to and from a visual inspection system or another part of the system can be accomplished fast and simple, accordingly to the above paragraphs.

In an advantageous embodiment of the invention, each gripper arm comprises at least one, in particular two, gripper tips in order to apply the lateral force onto the lateral surface of the bottom container. Advantageously, the form of each gripper tip is designed in a stealth design. Thus, the quality of the visual inspection is considerably enhanced due to a reduction of unwanted reflections and back reflections from the gripper tips.

In a further advantageous embodiment, the system according to the invention comprises pushing means built to move the petri dish on the conveyor along the conveyor direction onto the plate of the elevator, wherein the plate is in its neutral position. This has the advantage that the movement of the petri dishes into the device onto the plate of the elevator can be performed by the pushing means, wherein the conveyor can be, for example, a customary table. In addition, a petri dish that has already been visually inspected can be automatically pushed off the plate of the elevator by a new petri dish being moved onto the plate of the elevator by the pushing means, wherein the plate is in its neutral position.

Advantageously, the system comprises a second sensor at the conveyor, wherein the second sensor is built to detect the petri dish being pushed by the conveyor drive or by the pushing means along the conveyor direction in direction of the device.

These and further advantageous embodiments of the invention will be explained based on the following description and the accompanying drawings. The person skilled in the art will understand that various embodiments may be combined.

BRIEF DESCRIPTION OF THE DRAWINGS

FIG. 3A shows in a perspective view a device according to the first embodiment of the invention.

FIG. 3B shows in a perspective view the device of FIG. 3A.

FIG. 4A shows in a perspective view the part of the system of FIG. 2B.

FIG. 4B shows in a perspective view the part of the system of FIG. 2B.

Detailed Description of Aspects of Some Example Embodiments

Figure 1:
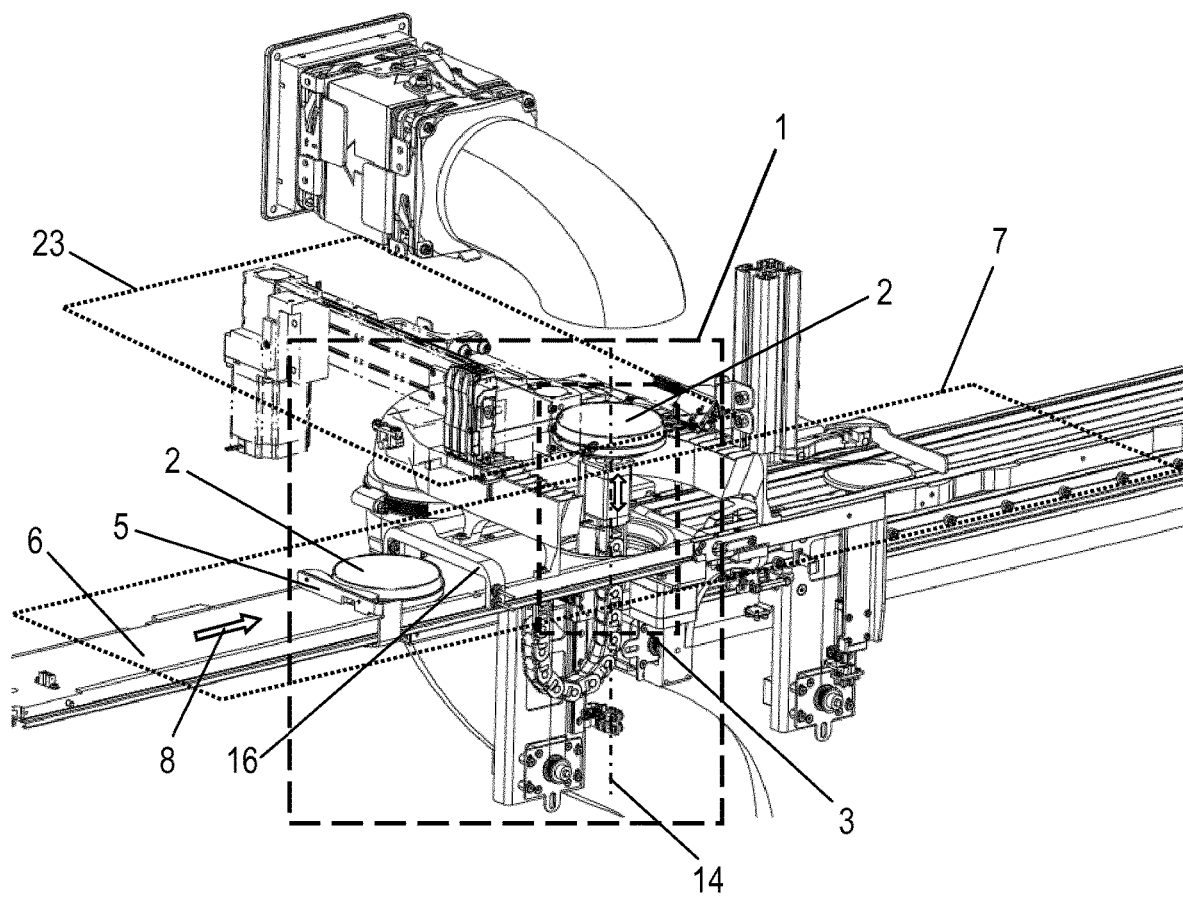
FIG. 1 shows in a perspective view a system according to a first embodiment of the invention.

FIG. 1 shows a system 1 for handling and centring of petri dishes 2 according to a first embodiment of the invention. The system 1 is part of a more comprehensive equipment for fully automated handling, visual investigation and sub-Sequent sorting of petri dishes 2.

The system 1 comprises a device 3 for centring of petri dishes 2, a gripper 4, not shown in FIG. 1, and pushing means 5 built to move the petri dishes 2 along a conveyor direction 8 on a conveyor plane 7 of a conveyor 6. The system 1 further comprises a second sensor 16 at the conveyor 6, which second sensor 16 is built to detect the petri dishes 2 being moved by the pushing means 5 along the conveyor direction 8. Advantageously, the system 1 is installed in a way that the conveyor plane 7 is substantially horizontal.

Figure 2A:
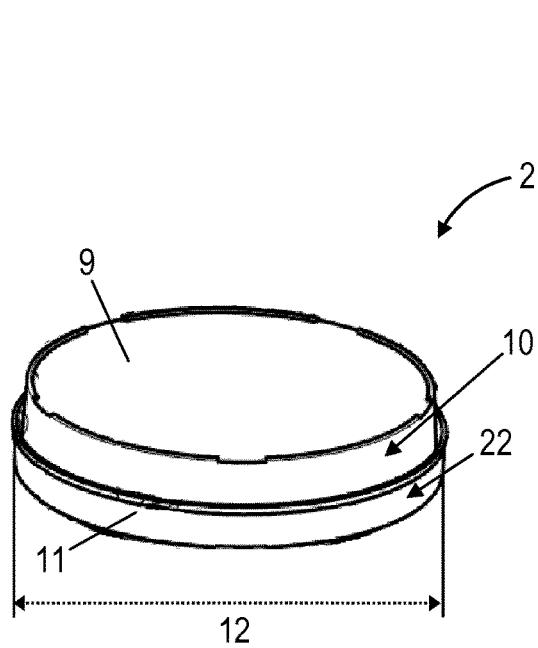
FIG. 2A shows in a perspective view a customary petri dish.

Each petri dish 2, as shown in FIG. 2A, consists of a bottom container 9 with a lateral surface 10 and a lid 11 with a lid diameter 12 and a peripheral surface 22. The peripheral surface 22 of the lid 11 overlaps the lateral surface 10 of the bottom container 9. The petri dishes 2 are handled with the lid 11 down and the bottom container 9 upwards throughout the whole system 1. Of course, the system 1 can also handle the petri dishes 2 with the bottom container 9 down and the lid 11 upwards.

The petri dishes 2 are advantageously of cylindrical form, involving a cylindrical bottom container 9 and a cylindrical lid 11.

Figure 2B:
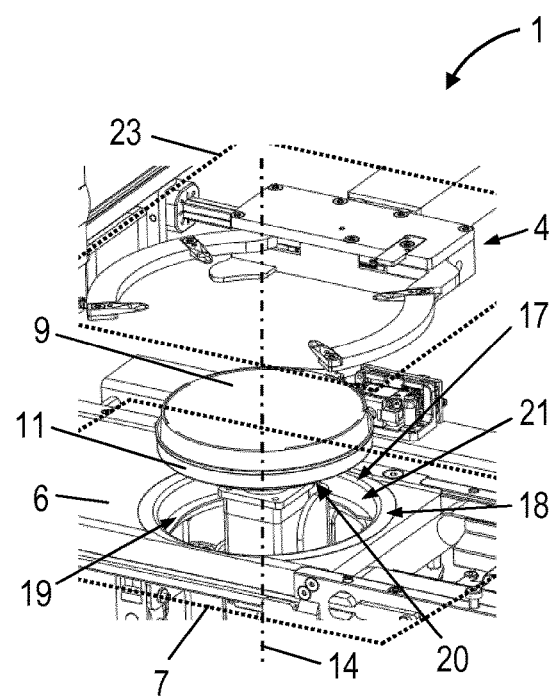
FIG. 2B shows in a perspective view a part of the system according to the first embodiment of the invention.

FIG. 2B shows a part of the system 1, which part comprises the device 3 according to the first embodiment of the invention. This part of the system 1 and the device 3 are also shown in FIGS. 3A to 4B. The device 3 comprises an elevator 13 with an elevator axis 14, which is substantially rectangular to the conveyor plane 7, and an elevator drive 15. The elevator drive 15 is built to move the elevator 13 along the elevator axis 14. The device 3 comprises further the conveyor 6, which holds the petri dishes 2 on the conveyor plane 7 substantially rectangular to the elevator axis 14. In the present first embodiment, the conveyor can be seen as a customary plate on which the petri dishes 2 are moved along the conveyor direction 8 by the pushing means 5. Alternatively, the conveyor 6 could be a conveyor belt comprising a conveyor drive built to convey the petri dishes 2 on the conveyor plane 7 along the conveyor direction 8. Those skilled in the art will be aware of the fact that other configurations of the conveyor 6 may be used.

Concentrically along the elevator axis 14 the conveyor 6 comprises a frustoconical through-hole 17 tapering downwards, which is shown in detail in FIG. 2B. Advantageously, the circumferential form of the through-hole 17 around the elevator axis 14 is circular. The through-hole 17 tapers downward from a first opening 18, which is located in the conveyor plane 7 and is larger than the lid diameter 12 of the petri dish 2, throughout the conveyor 6 to a second opening 19, which is smaller than the lid diameter 12 of the petri dish 2. Thus, the through-hole 17 according to the invention, and consequently the device 3 according to the invention, can be used with any petri dish 2 of any size and form, as long as the lid diameter 12 of the petri dish 2 is smaller than the first opening 18 and larger than the second opening 19.

Alternatively, for example if the conveyor 6 is not thick enough in order to incorporate the whole through-hole 17 within its thickness, the through-hole 17 could be comprised by a ring or a similar element mounted at or to the conveyor 7 in the conveyor plane 7. Advantageously, such a ring or similar element could be replaceable in order to comprise a first opening and a second opening with different sizes or forms. Consequently, the through-hole 17 according to the invention, and consequently the device 3 according to the invention, can be used with any petri dish of any size and form.

The device 3 further comprises a first sensor 26 built to detect the petri dish 2 as soon as it is moved or pushed onto a substantially flat plate 20, which is in its neutral position, as shown in FIG. 3A. Thus, the device 3 can automatically detect the petri dish 2 received by the plate 20 in order to, for example, automatically start the centring of the petri dish 2.

"Substantially flat" in this context means that the petri dish 2 can be moved or pushed onto the plate 20, for example by the pushing means 5, without any appreciable resistance from the plate 20, wherein the plate 20 needs to be in a neutral position located in the conveyor plane 7.

Advantageously, the form of the plate 20 follows the form of the through-hole 17, which may be circular, whereas the diameter of the plate 20 is beneficially but not necessarily smaller than the second opening 19 of the through-hole 17.

The elevator drive 15 is built rotate the plate 20 around the elevator axis 14 and simultaneously move the plate 20 from the neutral position downwards along the elevator axis 14 into a first position. Since the rotation, which can be performed very fast, and the downward movement of the plate 20 are being executed simultaneously, the petri dish 2 can be centred in a very fast, simple and safe way. Herby, during the rotation and the simultaneous downward movement of the plate 20, the peripheral surface 22 of the lid 11 touches an inner surface 21 of the through-hole 17 with its, in accordance to the elevator axis 14, peripherally outermost points. Thus, the petri dish 2 is centred in accordance to the elevator axis 14 during the rotation and the simultaneous downward movement of the plate 20 inside the through-hole 17. As soon as the petri dish 2 rests with its weight on the inner surface 21 of the through-hole 17, the plate 20 reaches the first position and the elevator drive 15 stops the rotation and the downward movement of the plate 20. This situation is shown in FIG. 3B.

In a next step or in another step, which is shown in FIG. 4A, the elevator drive 15 is built to move the plate 20 from the first position and via the neutral position upwards through the through-hole 17 into a second position. The second position of the plate 20 is reached as soon as the lateral surface 10 of the bottom container 9 lies in a gripper plane 23.

In the present first embodiment of the invention, the gripper 4 is movably arranged in the gripper plane 23, for example by a gripper drive, not shown in the figures. The gripper 4 can comprise two gripper arms 24 movable in the gripper plane 23 towards each other. The gripper arms 24 can each comprise two gripper tips 25. The gripper 4 is built to receive the bottom container 9 of the petri dish 2 from the plate 20 in its second position. Hereby, the gripper drive moves the gripper arms 24 towards each other and applies a lateral force with the gripper tips 25 onto the lateral surface 10 of the bottom container 9. This situation is show in FIG. 4B, wherein the plate 20 carrying the lid 11 is in its neutral position. Those skilled in the art will be aware of the fact that other configurations of gripper arms 24 or gripper tips 25 may be used.

Advantageously, the form of each gripper tip 25 is designed in a stealth design. "Stealth design" means that the gripper tips 25 are designed to function with the visual analysis tool. The special surface shape of the gripper tips 25 deflects light away from the camera of the visual analysis tool, so that there are no unwanted reflections in the camera image. The "special surface shape" of the gripper tips 25 describes a surface with multiple flat facets, similar to the outer shell design of stealth planes. In addition, these facets are coated with a black and highly absorbing material or thin film in order to reduce back reflections.

As a next step or in another step, for example, the petri dish 2 can be moved by the gripper drive into a visual analysis tool, such as an automated microscope, for visual analysis. Herby, the gripper 4 may move back or forth, advantageously only within the gripper plane 23, for example out of or into the respective image plane of FIGS. 3A to 4B. Alternatively, the gripper 4 may rotate within the gripper plane 23 to move the petri dish 2. Of course, the gripper may also move the petri dish 2 upwards or downwards along the elevator axis 14 or along a direction parallel to the elevator axis 14. Nevertheless, in terms of a fast and save handling of the petri dish 2, it will appear obvious to those skilled in the art that as few directional changes and as short handling distances as possible are advantageous. In this context, the system 1 as according to the invention advantageously enables to handle and centre the petri dishes 2 only along the conveyor direction 8 within the conveyor plane 7, along the elevator axis 14, and within the gripper plane 23.

As a next step or in another step, the elevator drive 15 is built to move the plate 20 from its second position downwards into its neutral position.

As a next step or in another step, the petri dish 2 may be moved or processed further. Alternatively, the elevator drive 15 may move the plate 20 from its second position downwards into its neutral position while the petri dish 2 is visually analyzed by the visual analysis tool. Thus, in order to speed up the processing, a second petri dish 2 may be simultaneously moved onto the plate 20 and be centred while the first petri dish 2 is visually analyzed.

Summarizing, a method for a fast automated centring and handling process of a high number of petri dishes 2 according to the invention may be accomplished by processing the following steps:

The pushing means 5 move the petri dish 2 on the conveyor plane 7 along the conveyor direction 8.

The second sensor 16 detects the currently moved petri dish 2 and initializes the elevator drive 15 to move the plate 20 into its neutral position.

The pushing means 5 move the petri dish 2 onto the plate 20 of the elevator 13.

The first sensor 26 detects the petri dish 2 being received by the plate 20 and initializes the elevator drive 15 to start the centring procedure.

The elevator drive 15 rotates the plate 20 and simultaneously moves the plate 20 downwards along the elevator axis 14 through the through-hole 17 until the plate 20 is in a first position, which is reached as soon as the petri dish 2 rests with its weight on the inner surface 21 of the through-hole 17. The petri dish 2 is now centred in accordance to the elevator axis 14.

The elevator drive 15 moves the plate 20 from the first position and via the neutral position upwards along the elevator axis 14 through the through-hole 17 until the plate 20 is in the second position, which is reached as soon as the lateral surface 10 of the bottom container 9 lies in the gripper plane 23 of the gripper 4.

The gripper 4 takes over the bottom container 9 of the petri dish 2 from the plate 20 by the gripper arms 24, while the lid 11 stays on the plate 20.

The gripper 4 moves the bottom container 9 of the petri dish 2 in the gripper plane 23, for example forward out of the image plane of FIG. 4B, into the visual analysis tool.

The visual analysis of the first petri dish 2 is finished and the gripper 4 moves the bottom container 9 of the petri dish 2 back onto the lid 11 on the plate 20.

The system 1 initializes the pushing means 5 to move another petri dish 2 on the conveyor plane 7 along the conveyor direction 8.

The second sensor 16 detects the currently moved second petri dish 2 and initializes the elevator drive 15 to move the plate 20 into its neutral position.

The pushing means 5 move the second petri dish 2 onto the plate 20 of the elevator 13, wherein the first petri dish 2 is pushed from the plate 20 by the second petri dish 2.

The first sensor 26 detects the second petri dish 2 being received by the plate 20 and initializes the elevator drive 15 to start the centring procedure.

The centring and handling process continues accordingly.

A system or a device according to a further embodiment of the invention could be adopted to handle and/or centre petri dishes 2 within, to or from other analysis tools or equipment, such as a chemical composition analysis tool, an incubation system, an oven, a storage system, a sorting system, a weighting tool, radiation equipment such as X-Ray, IR or UV, labelling equipment in order to label the petri dishes 2, or similar systems.

A system or a device according to a further embodiment of the invention could be adopted to handle petri dishes of rectangular or quadratic form, involving a rectangular or quadratic bottom container and a rectangular or quadratic lid. In this case, the lid diameter is the diagonal of the rectangular or quadratic lid. Additionally the petri dishes could be of any random form, involving a bottom container having advantageously substantially the same form as the lid.

A system or a device according to a further embodiment of the invention could be adopted to handle and centre all kinds of similar flat and transparent or non-transparent containers or boxes with a lid, such as laboratory ware or boxes/containers containing chemical or biological material or electronic devices.

The invention claimed is:

1. A system comprising a petri dish and a device for centering the petri dish, which petri dish includes a bottom container with a lateral surface and a lid with a lid diameter, which device comprises an elevator with an elevator axis and an elevator drive, by which the elevator is movable along the elevator axis, and a conveyor, which holds the petri dish on a conveyor plane rectangular to the elevator axis, wherein the conveyor comprises concentrically along the elevator axis a frustoconical through-hole tapering downwards from a first opening, which is located in the conveyor plane and is larger than the lid diameter of the petri dish, to a second opening, which is smaller than the lid diameter of the petri dish, and that the elevator drive is operable to move a flat plate, which is configured to receive the petri dish, from a neutral position located in the conveyor plane downwards into a first position, which is reached as soon as the petri dish rests with its weight on the inner surface of the through-hole, wherein the elevator drive is operable to rotate the plate around the elevator axis in order to rotate the plate during a movement of the plate from the neutral position into the first position.

2. The system according to claim 1, wherein the elevator drive is operable to move the plate from the first position upwards through the through-hole and via the neutral position into a second position, which is reached as soon as the lateral surface of the bottom container lies in a gripper plane.

3. The system according to claim 2, wherein the elevator drive is operable to move the plate from the second position downwards into the neutral position.

4. The system according to claim 1, wherein the conveyor comprises a conveyor drive operable to convey the petri dish on the conveyor plane along a conveyor direction onto the plate.

5. The system according to claim 1, comprising a first sensor operable to detect the petri dish on the plate.

6. The system according to claim 1, wherein the conveyor comprises a ring mounted in the conveyor plane and comprising the through-hole, wherein the ring is configured to be replaceable.

* * * * *